United States Patent [19]

Cassimally

[11] 4,265,226
[45] May 5, 1981

[54] INCISION CLOSING METHOD

[76] Inventor: Khalil A. I. Cassimally, 403 Hayes Rd., Fort Pierce, Fla. 33450

[21] Appl. No.: 23,262

[22] Filed: Mar. 23, 1979

[51] Int. Cl.³ ............... A61B 17/08; F16B 15/00; B25C 5/00
[52] U.S. Cl. .................. 128/1 R; 227/DIG. 1; 227/83; 227/108; 411/447; 128/335; 128/337; 411/447; 411/471
[58] Field of Search ........... 128/325, 335.5, 335, 128/336, 337; 227/DIG. 1, 12, 25, 83, 108; 85/49

[56] References Cited

U.S. PATENT DOCUMENTS

| 268,632 | 12/1882 | Danforth | 128/337 |
| 816,026 | 3/1906 | Meier | 128/335.5 |
| 1,315,369 | 9/1919 | Klinge | 128/337 |
| 2,811,971 | 11/1957 | Scott | 128/335 |
| 3,570,497 | 3/1971 | Lemole | 128/335.5 |
| 3,716,058 | 2/1973 | Tanner, Jr. | 128/337 |

Primary Examiner—Robert W. Michell
Assistant Examiner—C. W. Shedd
Attorney, Agent, or Firm—Beaman & Beaman

[57] ABSTRACT

The invention relates to an improved method and means for closing an incision with surgical clips wherein the clips have a preformed preliminary skin hooking portion and a portion deformable on application to hook the skin on the opposite side of the incision whereby the clip becomes a surgical tool for holding the skin on one side of the incision while the closing of the incision by the clip is being carried out.

1 Claim, 13 Drawing Figures

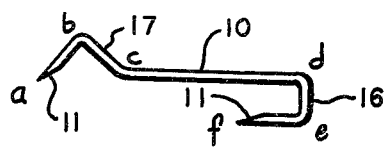
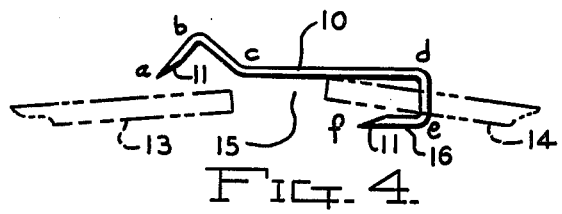
FIG. 1.   FIG. 4.
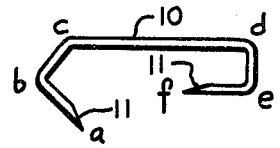
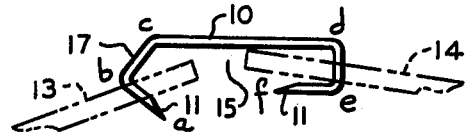
FIG. 2.   FIG. 5.
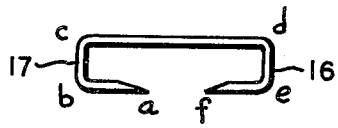
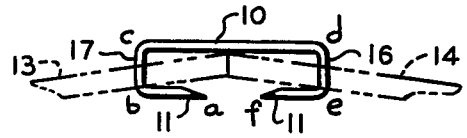
FIG. 3.   FIG. 6.
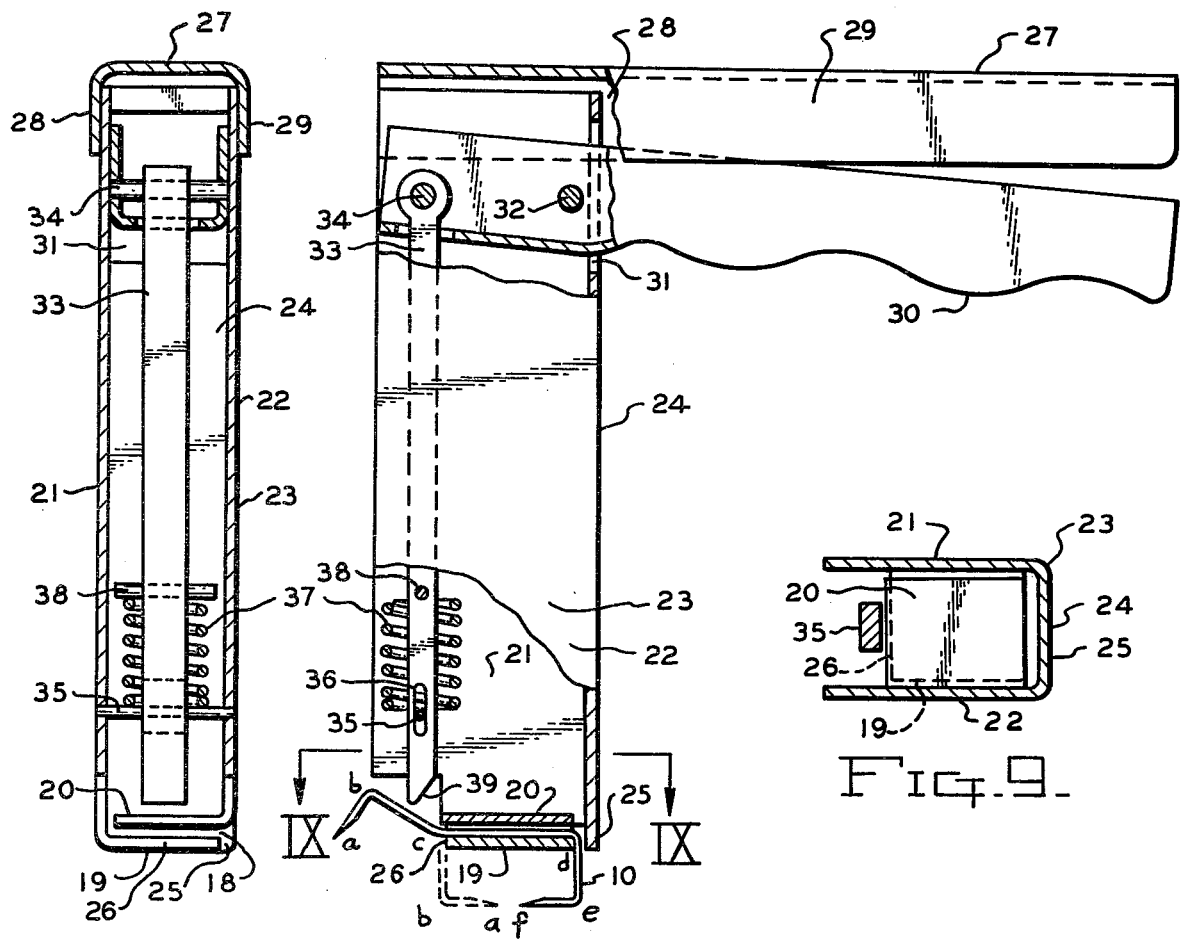
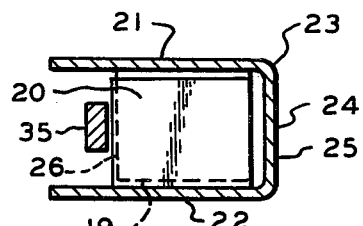
FIG. 8.   FIG. 7.   FIG. 9.

INCISION CLOSING METHOD

BACKGROUND OF THE INVENTION

Metal surgical clips, staples, clamps and the like have been in use for many years to close an incision as a substitute for or in association with stitches and sutures. Such prior art devices have skin piercing terminals connected by a central portion. To close the incision, the central portion of the clip is deformed causing the skin piercing terminals to simultaneously approach each other to pierce the skin and close the incision. See Van Schott U.S. Pat. No. 721,480.

In the use of the aforesaid prior art devices, the surgeon usually holds the skin on both sides of the incision by a pair of forceps held in one hand, while operating the clip applicator with the other hand. As a result the opposing surfaces of the skin often slips between the surgeon's forceps and the application of clips to close the incision is hindered.

SUMMARY OF THE INVENTION

According to the method and apparatus of the present invention, the surgical clip becomes a tool for holding the skin on one side of the incision, while the clip applicator is performing the incision closing operation on the skin on the other side of the incision being positioned by a pair of forceps held by the other hand of the surgeon. In lieu of deforming the central portion of the clip to cause the skin piercing terminal ends of the clip to approach each other, one such end is preformed, preferably to its final configuration relative to the central portion of the clip. With the clip positioned in the applicator, with the preformed end exposed, the surgeon may manipulate the applicator to hook the skin on one side of the incision with the preformed end.

In its simplest form, the clip is non-nesting in form and preformed prior to being inserted in the applicator. Thus one end of the clip has the final form of the clip as applied in use, while the other end is deformed in the applicator to complete the final form of the clip in use. However, to permit magazine feeding of the clips, the clips may be of nesting form with preforming of one end of the clip in the applicator prior to the use of such end as a tool by the surgeon.

BRIEF DESCRIPTION OF THE DRAWINGS

FIG. 1 is a side elevational view of the surgical clip having a preformed end,

FIG. 2 is a view similar to FIG. 1 with the clip end opposite the preformed end being partially deformed, FIG. 3 is a view similar to FIG. 1 with the clip shown in the form it takes in use to close an incision, FIG. 4 shows the clip in the form of FIG. 1 with the skin on one side of the incision hooked upon the preformed end, FIG. 5 shows the clip in the form of FIG. 2 with the skin on both sides of the incisions pierced, FIG. 6 shows the clip in the form of FIG. 3 with the ends of similar form and the incision closed by the clip, FIG. 7 is a side elevational view of the applicator with a clip shown in place prior to deformation, FIG. 8 is an end view of FIG. 7 taken from the left, FIG. 9 is a cross sectional view taken on line IX—IX of FIG. 7.

DESCRIPTION OF THE PREFERRED EMBODIMENT

Figure 10:
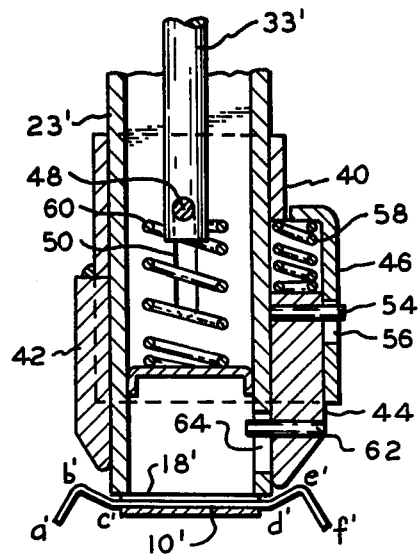
FIG. 10 is a fragmentary vertical section of a modification for forming both ends of the clip with the applicator, in the fully up position.
Figure 11:
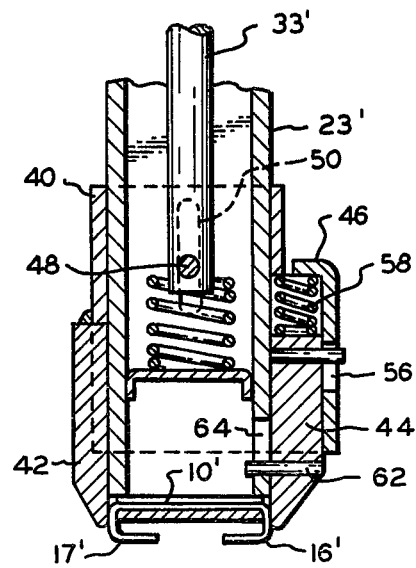
FIG. 11 is a view similar to FIG. 10 with the applicator in the fully down position.

In FIG. 1 the clip 10 is shown of suitable flat or round deformable metal stock pointed at 11 to pierce the skin. The length c-d represents the central portion of the clip 10; the length d-e-f, the preformed end; and the length a-b-c, the clip end to be deformed by the applicator.

In FIG. 2 the clip is shown with the clip length a-b-c partly deformed to engage and pierce the skin on one side of the incision. The form of the clip in FIG. 3 is the completed shape with the clip 10 closing the incision.

FIGS. 4, 5 and 6 show the same clip form as FIGS. 1, 2 and 3, respectively, with the order of association of the skin 13 and 14 on opposite sides of the incision 16 being illustrated. In FIG. 4, the preformed end 16 defined by the length d-e-f is shown hooked into the skin 14. In FIG. 4, deformation of the length a-b-c defining the end 17 has resulted in the skin 13 being pierced by the end 17. With the deformation of the length a-b-c completed the end 17 takes the form of the preformed end 16 as shown in FIG. 6, closing the incision 15.

Referring to the FIGS. 7–9, the clip 10 is shown in the form of FIG. 1 disposed in the slot 18 defined by the inturned lower parts 19 and 20 of the side portions 21 and 22 of the upright body part of the applicator 23. As shown in FIG. 9, the part 23 is U-shaped in cross section with the portion 24 connecting the side portions 21 and 22. In providing the slot 18, the lower end 25 of the portion 24 is extended below the slot 18 to close one end of the slot 18 and form an abutment for the length d-e of the end 16 of the clip 10. It will be understood that the width of the part 19 approximate the length c-d of the clip 10 whereby the outer edge 26 of the part 19 constitutes a fulcrum about which the length a-c-b of the clip 10 is deformed by bending. The width of the part 20 is such that it extends beyond the edge 26 a distance approximately the thickness of the clip 10.

Rigid with the upright body part of the applicator 23 is a right angle handle portion 27 of U-shaped section having side portions 28 and 29 welded or otherwise fixed to the sides 21 and 22. To complete the handle, a grip portion 30 is provided, also U-shaped in section, extending through an opening 31 in the portion 24 and having a close fit for pivotal movement between the portions 21 and 22 above the pivot pin 32. Opposite ends of the pin 32 are supported in the portions 21 and 22.

To rotate, by bending, the length a-b-c of the clip 10 about the edge 26, a cam rod 33 is provided, being attached at its upper end to the pin 34 carried at its outer ends in the portion 30. A pin 35 in the slot 36 of the rod 33 is carried at its end in the portions 21 and 22 to control the path of movement of the rod 33 and to provide a seat for the compression spring 37. A cross pin 38 carried by the rod 33 provides the upper seat for the spring 37.

The cam rod 33 has an angular cam surface 39 at its lower end which abuts the length b-c of the clip 10 and wipes the same about the edge 26 into the position shown in dotted outline in FIG. 7. Movement of the rod 33 results from movement of the grip portion 30 counter-clockwise compressing the spring 37 and lowering the rod 33 to project the cam surface 39 into the dotted line position of FIG. 7.

In the modification of FIGS. 10–13 the clip 10' has length portions a'-b'-c' corresponding to the length a-b-c of clip 10 defining the end 17, length portions c'-d' corresponding to the central portion c-d of the clip 10, and length portions d'-e'-f' corresponding to the length d-e-f of clip 10 defining the end 16. With a clip of the form of the clip 10' as shown in full line in FIG. 10, the clip 10' may be nested with similar clips in a suitable magazine (not shown) and fed one at a time in a well known manner into the slot 18'.

Figure 12:
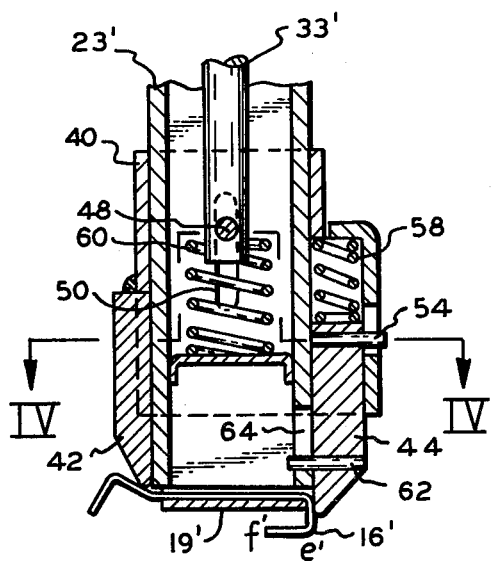
FIG. 12 is similar to FIG. 10 with the applicator in an intermediate position.
Figure 13:
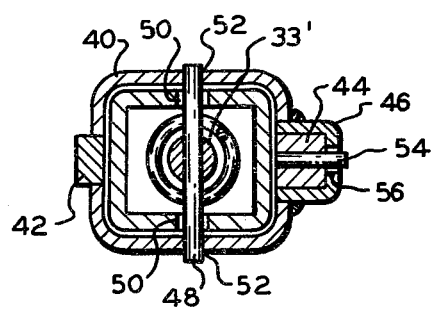
FIG. 13 is a cross sectional view taken on line XIII—XIII of FIG. 12.

To preform the length d'-e'-f' of the clip 10' to provide the end 16' in the form shown in FIG. 12, a sleeve 40 is supported for free sliding vertical movement on the upright body portion of the applicator 23'. Cam 42 is fixed to the sleeve 40 and has unitary movement therewith to bend the end 17' of the clip 10' from the position of FIG. 10 into the position of FIG. 12. Opposite the cam 42 is a cam 44 supported in the sleeve 40 for both unitary and relative vertical movement within a housing 46.

Movement is imparted to the sleeve 40 through the rod 33' which may be actuated in the manner of the rod 33. A pin 48 camed by the rod 33' projects through slots 40 with its opposite end being received in holes 52 in the sleeve 40.

A pin 54 camed by the cam 44 and acting in a slot 56 of the housing 46 resist the action of the compression spring 58 to hold the cam 44 in the position shown in FIG. 10 relative to the sleeve 40. A second compression spring 60 supported on a bracket fixed in the upright body portion of the applicator 23' acts upon the rod 33' through the pin 48 to raise the sleeve 40, as shown in FIG. 10, to the extent permitted by the pin 62 camed by the cam 44 and operating in the slot 64.

With the clip 10' disposed on the part 19' and in the form it may be magazine fed, the rod 33' is moved downwardly as viewed in FIG. 10. As the nose of the cam 44 is leading the nose of the cam 42, the end 16' of the clip is bent into the form shown in FIG. 12. During this movement of the cam 44 the spring 58 is resisting relative movement between the cam 44 and sleeve 40.

When the pin 62 abuts the lower end of the slot 64 the cam 44 is arrested with its nose backing up the bent end 16' of the clip 10'. At this point the spring 58 is resisting further downward movement of the sleeve 40. This resistance is telegraphed to the user of the applicator.

As the end 16' is now in a position to pierce and hold the skin at one side of the incision, manipulation of the applicator 23' will accomplish this act. Thereafter further pressure is exerted on the rod 33' overcoming the resistance of the spring 58 to lower the sleeve 40 further and bring the cam 42 into the position shown in FIG. 11 to complete the deformation of the clip 10' by bending the end 17' into its final form.

It will be understood that the modification of FIGS. 10–13 is capable of bending both ends of the clip 10', in sequence, upon an interrupted downward movement of the rod 33' upon manipulation of the handle of the applicator such as shown in FIG. 7. In practice, the end 16' of the clip 10' will be bent by the first part of the downward movement of the rod 33'. The formed end of the clip 10' is then used to pierce and hold the skin on one side of the incision. Thereafter the downward movement will continue to deform the end 17', to pierce the skin on the opposite side of the incision and to close the incision all during the final position of the interrupted movement of the rod 33'.

I claim:

1. A method of closing an incision with a deformable clip, said clip initially comprising a hook portion which extends into a shank portion such that the whole is generally J-shaped, said clip having tissue piercing portions at the free ends of said hook and shank portions whereby the closing of said incision comprises:
    piercing the tissue adjacent one side of said incision with the piercing portion of said hook portion,
    inserting said hook portion in said tissue and thereby holding same,
    deforming said shank portion so as to pierce the tissue adjacent the opposed side of said incision with the piercing portion of said shank portion,
    further deforming said shank portion such that said clip is transformed to be generally C-shaped;
    said further deformation of said shank acting to gather said opposed tissues and thereby close the incision.

* * * * *